United States Patent [19]

Schoolman

[11] Patent Number: 5,677,728
[45] Date of Patent: Oct. 14, 1997

[54] STEREOSCOPIC VIDEO TELECOMMUNICATION SYSTEM

[75] Inventor: Arnold Schoolman, Kansas City, Mo.

[73] Assignee: Schoolman Scientific Corporation, Kansas City, Mo.

[21] Appl. No.: 202,499

[22] Filed: Feb. 28, 1994

Related U.S. Application Data

[63] Continuation-in-part of Ser. No. 91,461, Jul. 14, 1993, which is a continuation of Ser. No. 615,218, Nov. 19, 1990, abandoned, which is a continuation-in-part of Ser. No. 229,472, Aug. 8, 1988, abandoned, which is a continuation-in-part of Ser. No. 179,059, Apr. 8, 1988, abandoned, which is a continuation-in-part of Ser. No. 935,066, Nov. 21, 1986, Pat. No. 4,737,972, which is a continuation of Ser. No. 671,436, Nov. 14, 1984, abandoned, which is a continuation-in-part of Ser. No. 616,385, Jun. 1, 1984, Pat. No. 4,559,555, which is a continuation-in-part of Ser. No. 351,917, Feb. 24, 1982, abandoned.

[51] Int. Cl.$^6$ ........................................................ H04N 7/14
[52] U.S. Cl. ................................. 348/19; 348/14; 348/45; 379/96
[58] Field of Search .................................... 348/13, 14, 15, 348/16, 17, 18, 19, 42, 43, 46, 47, 48, 51, 52, 53; 379/96, 94, 93

[56] References Cited

U.S. PATENT DOCUMENTS

| | | |
|---|---|---|
| 2,955,156 | 10/1960 | Heilig . |
| 4,310,849 | 1/1982 | Glass . |
| 4,367,548 | 1/1983 | Cotten, Jr. et al. . |
| 4,441,180 | 4/1984 | Schussler . |
| 4,627,105 | 12/1986 | Ohashi et al. . |
| 4,631,580 | 12/1986 | Taube et al. ............................. 348/47 |
| 4,636,866 | 1/1987 | Hattori . |
| 4,706,117 | 11/1987 | Schoolman . |
| 4,743,965 | 5/1988 | Yamada et al. .......................... 348/43 |
| 4,769,833 | 9/1988 | Farleigh et al. . |
| 4,856,045 | 8/1989 | Hoshina . |
| 4,884,131 | 11/1989 | Chevion et al. ......................... 348/43 |
| 4,891,694 | 1/1990 | Way . |
| 4,928,301 | 5/1990 | Smoot . |
| 4,932,047 | 6/1990 | Emmons et al. . |
| 4,933,755 | 6/1990 | Dahl et al. . |
| 4,945,404 | 7/1990 | Miller . |
| 4,979,028 | 12/1990 | Minematsu et al. . |
| 4,982,278 | 1/1991 | Dahl et al. . |
| 4,985,911 | 1/1991 | Emmons et al. . |
| 5,048,077 | 9/1991 | Wells et al. . |
| 5,063,587 | 11/1991 | Semasa et al. . |
| 5,079,627 | 1/1992 | Filo . |
| 5,111,498 | 5/1992 | Guichard et al. . |
| 5,157,491 | 10/1992 | Kassatly .................................. 348/16 |
| 5,164,980 | 11/1992 | Bush et al. . |
| 5,181,107 | 1/1993 | Rhoades . |
| 5,193,000 | 3/1993 | Lipton et al. ........................... 348/51 |
| 5,239,373 | 8/1993 | Tang et al. .............................. 348/14 |
| 5,261,404 | 11/1993 | Mick et al. .......................... 364/413.13 |
| 5,515,268 | 5/1996 | Yoda ..................................... 364/401 |

*Primary Examiner*—Stella Woo
*Attorney, Agent, or Firm*—Litman, McMahon and Brown, L.L.C.

[57] ABSTRACT

A stereoscopic video telecommunication system includes a fiberoptic based wideband switching network interconnecting wideband subscriber stations and narrowband subscriber stations. A wideband station includes a stereoscopic video receiver along with a stereophonic audio receiver for respectively displaying and playing stereo video and audio signals received by way of the network. The wideband station may also include a stereoscopic video source such as a pair of stereoscopic video cameras along with a stereophonic pair of microphones. The wideband station may also include narrowband devices such as a conventional telephone, a computer, and a facsimile machine. Connections between stations on the network are established by dialing another station and transferring the desired signal, including stereoscopic video signals. Preferably, the signals are converted to a digital format and, especially for stereoscopic video signals, data compressed to conserve network overhead.

24 Claims, 5 Drawing Sheets

STEREOSCOPIC VIDEO TELECOMMUNICATION SYSTEM

CROSS-REFERENCE TO RELATED APPLICATIONS

This a continuation-in-part of Ser. No. 08/091,461 filed Jul. 14, 1993 for STEREOSCOPICALLY DISPLAYED THREE DIMENSIONAL MEDICAL IMAGING which is a continuation of Ser. No. 07/615,218 filed Nov. 19, 1990, abandoned, which is a continuation-in-part of Ser. No. 07/229,472 filed Aug. 8, 1988 for STEREOSCOPICALLY DISPLAYED THREE DIMENSIONAL MEDICAL IMAGING, abandoned, which is a continuation-in-part of Ser. No. 07/179,059 filed Apr. 8, 1988 for HIGH FIDELITY STEREOSCOPIC COMBINED LCD AND CRT TELEVISION DISPLAY, abandoned, which is a continuation-in-part of Ser. No. 06/935,066 filed Nov. 21, 1986 for STEREOSCOPIC FLUOROSCOPE ARRANGEMENT, now U.S. Pat. No. 4,737,972, which is a continuation of Ser. No. 06/671,436 filed Nov. 14, 1984, abandoned, which is a continuation-in-part of Ser. No. 06/616,385 filed Jun. 1, 1984 for STEREOSCOPIC REMOTE VIEWING SYSTEM, now U.S. Pat. No. 4,559,555 which is a continuation-in-part of Ser. No. 06/351,917 filed Feb. 24, 1982 for PORTABLE REMOTE TERMINAL WITH HEAD HELD DISPLAY, abandoned, all such applications being incorporated herein by reference.

BACKGROUND OF THE INVENTION

The present invention relates to communication systems and, more particularly, to a system with the capability of communicating stereoscopic video signals, along with stereophonic audio signals, over telecommunication lines.

Common voice grade telephone lines have been utilized for a number of years in connection with the transmission and reception of signals other than strictly voice derived signals. Present day voice grade telephone lines are metallic conductors and have a standard bandwidth of about 300 to 3400 Hz. This narrow bandwidth imposes limitations in the use of conventional voice grade telephone lines for purposes other than voice communication and relatively slow data communications. Attempts to provide visual communication between conversing parties have been limited by the narrow bandwidth of conventional telephone lines to relatively slow-scan pictures, essentially still pictures which are updated at relatively long intervals.

In some senses, the use of full color in image recording and display is looked upon as an unnecessary luxury. However, to a great degree, color can often provide a means for optically distinguishing between parts of an image which would have similar gray tones in a black and white image. Thus, color adds picture detail which can convey important information about a recorded scene. In a similar manner, stereoscopic recording and display of an image can convey important pictorial information which may otherwise be missed in a monoscopic rendering. This can be especially true in analyzing images of unknown subjects. The value of stereoscopy has long been recognized in the analysis of reconnaissance photographs. It is also true in areas such as diagnostic medical imaging.

One of the problems of recording, communicating, and displaying full color, full motion, and stereoscopic images is that each enhancement of the pictorial detail of a recorded image greatly increases the amount of data which represents the image and which must be processed and communicated. Although there are known video data compression techniques which would allow full motion color video signals to be communicated over conventional voice grade lines, such techniques are inherently "lossy". While such loss in picture fidelity may be tolerable for entertainment types of imaging, such loss of detail is often intolerable in more serious types of imaging, such as medical and scientific imaging.

The emergence of fiber optics as a communication medium is projected to provide many advantages over conductive wires in signal communications including lower signal loss over a given distance, much higher immunity to interference from external sources, very low radiation of interference, and much greater signal bandwidth. There are proposals for wideband switching networks which are expected to eventually replace the narrow bandwidth wiring and switching equipment of present day telephone systems. There are also proposals for integrating present day telephone communication systems with cable television systems and additionally with other services such as data communications and interactive data communications.

SUMMARY OF THE INVENTION

The present invention provides a stereoscopic video telecommunication system for intercommunicating wideband signals, including stereoscopic video signals and stereophonic audio signals, over a wideband switching network. In general, each subscriber installation of the wideband network may include a stereo audio/video source, a stereo audio/video receiver device, device interfaces which convert between analog signals for the source and receiver and digital signals for the network, and a network interface which interfaces digital electrical signals of the subscriber installation to the digital optical signals which are communicated over the wideband switching network. Each subscriber installation may also include data communication devices, such as computers, facsimile (fax) machines, or the like, and a conventional telephone for conventional telephonic communications. Some subscriber installations may only use narrowband services, such as telephone and data communication services, and may be billed at a lower rate. Other installations may only use monoscopic video capabilities.

The subscriber installations or stations cooperate with a wideband switching network which is fiber optic based. A switching network controller, such as a large high throughput computer, controls the routing of signals from calling stations to called stations. Additionally, the controller records network usage for billing purposes. The switching network incorporates signal amplifiers for maintaining signal strengths along the trunks and branches of the communication lines of the network.

OBJECTS AND ADVANTAGES OF THE INVENTION

The principal objects of the present invention are: to provide improved and more versatile telecommunication capabilities; to provide, particularly, a system having the capability of communicating stereoscopic video signals along with stereophonic audio signals between remote stations interconnected by a wideband telecommunication network; to provide such a system including a stereoscopic video source at one or more of the stations of the network, such as stereoscopic video camera pairs, stereoscopic video storage devices, computer generated stereoscopic images, and the like to provide stereoscopic video signals representing still and moving stereoscopic images; to provide such a system including video display devices, particularly stereoscopic video display devices, at one or more of the stations of the network; to provide such a system including head-worn stereoscopic video display devices; to provide such a system including stereophonic audio sources at some of the stations, including sources of stereophonic audio signals associated with stereoscopic video signals; to provide such a system including stereophonic audio receivers at some of the stations to decode and play stereophonic audio signals received from other stations; to provide such a system including analog to digital converters (ADC's) to convert analog signals from the video and audio sources to digital signals for communication on the network and digital to analog converters (DAC's) to convert digital signals received over the network to analog signals for use by the video displays and audio play devices; to provide such a system having the capability of communicating digital data over the network, such as text data, facsimile data, and the like; to provide such a system having the capability of carrying conventional voice telephone conversations over the network; to provide such a system capable of carrying multiple channels of signals representing video images for purposes such as full motion video conferencing between multiple stations on the network; and to provide such a stereoscopic video telecommunication system which is economical to manufacture, which is versatile in operation, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification, include exemplary embodiments of the present invention, and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
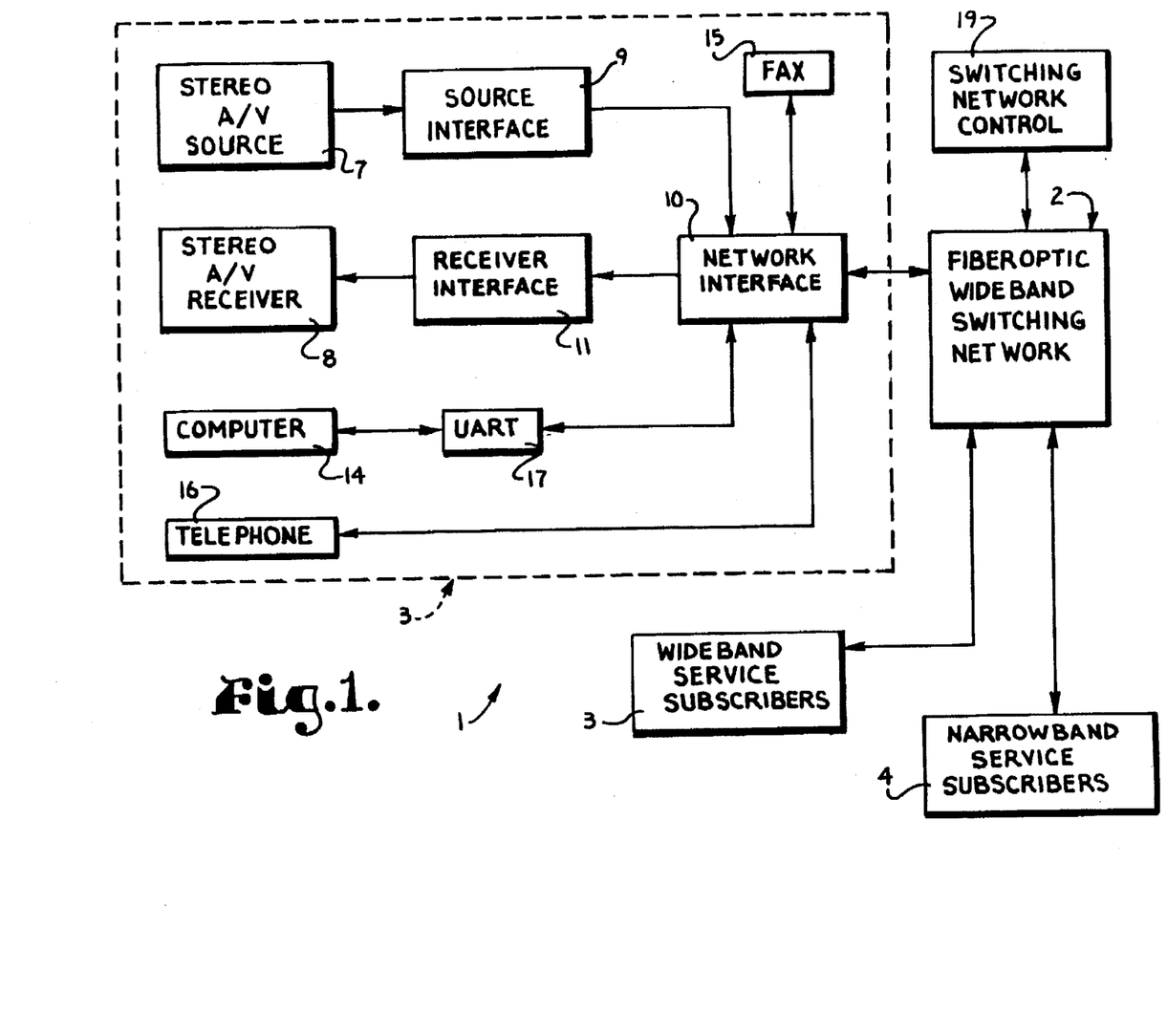
FIG. 1 is a block diagram illustrating the principal components of a stereoscopic video telecommunication system embodying the present invention.

Referring to the drawings in more detail:

The reference numeral 1 generally designates a stereoscopic video telecommunication system which embodies the present invention. In general, the system 1 provides duplex wideband communications over a wideband switching network 2 between wideband service subscriber stations 3 and provides duplex narrowband communications between wideband stations 3, between wideband stations 3 and narrowband service subscriber stations 4, and between narrowband stations 4.

Each wideband subscriber station 3 includes wideband devices, such as a stereo audio/video (A/V) source 7 and a stereo audio/video (A/V) receiver 8. The A/V source 7 generates a stereoscopic video signal representing a stereoscopic view of an image sensed by the A/V source 7 and additionally generates a stereophonic audio signal. The A/V receiver 8 is capable of displaying stereoscopic images derived from a stereoscopic video signal and audibly playing a stereophonic audio signal. The A/V source 7 is coupled to the network 2 by source interface circuitry 9 and network interface circuitry 10. The A/V receiver 8 is coupled to the network 2 by receiver interface circuitry 11 and the network interface circuitry 10. The wideband station 3 may also include narrowband devices, such as a computer 14, a facsimile machine or fax 15, and a conventional telephone 16, all of which are interfaced through the network interface circuitry 10. The computer 14 is coupled to the network interface circuitry 10 by means of a universal asynchronous receive/transmit device or UART 17, which may be incorporated in a conventional modem.

The narrowband stations 4 may incorporate a conventional telephone 16 along with network interface circuitry 10. Additionally, other narrowband devices may be utilized, such as a computer 14 and a fax 15. Thus, narrowband communications, such as conventional telephone conversations, are possible between wideband stations 3 and other wideband stations 3, between wideband stations 3 and narrowband stations 4 and between narrowband stations 4, and between narrowband stations 4 and other narrowband stations 4.

The wideband switching network 2 provides point-to-point communications between the subscriber stations 3 and 4 connected to the network 2 under the control of a switching network controller 19, which is a digital computer. Connections between the various subscriber stations 3 and 4 are established on a dial-up basis by use of telephone sets 16 or by use of computers 14, in the manner of conventional telephone service. The controller 19 decodes dialed number codes to enable a communication link between the calling station and the called station. The subscriber stations 3 and 4 are interconnected to the network 2 by fiber optic media to provide wideband capabilities to all subscriber stations 3 and 4, although utilization of the wideband capabilities requires wideband devices at the subscriber stations.

The network 2 has the capability, within the bandwidth and throughput limits of the network 2, of providing a simultaneous connection between a single wideband station 3 and a plurality of wideband stations 3 to provide the capability of sending a single stereoscopic video signal to a plurality of receiving stations. Additionally, for video conferencing, the network 2 can simultaneously interconnect multiple wideband stations 3 to enable each participant in a conference to see the other participants. Additional details of wideband switching networks can be found in U.S. Pat. Nos. 4,441,180; 4,769,833; and 4,891,694 which are incorporated herein by reference.

Figure 2:
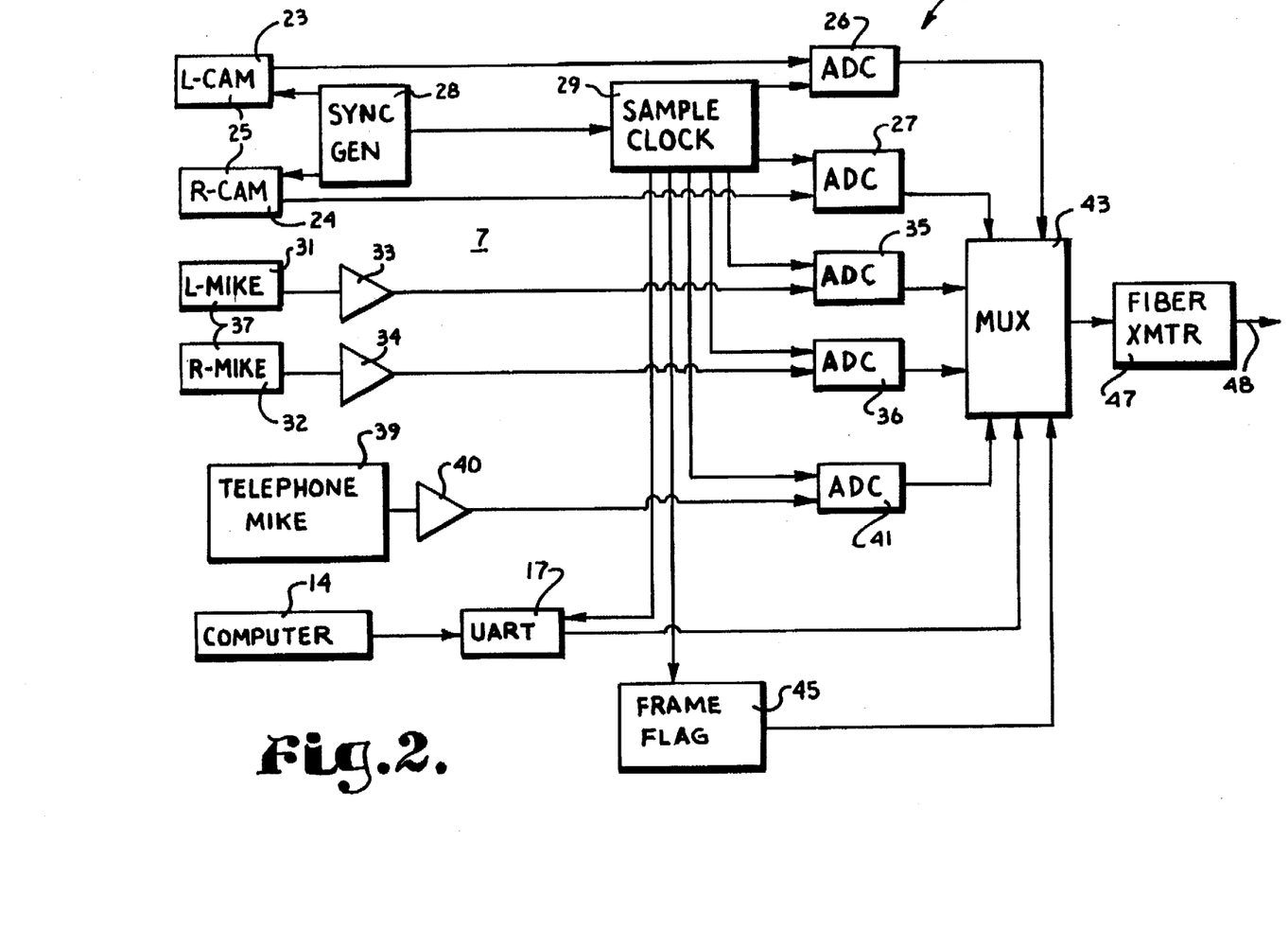
FIG. 2 is a block diagram illustrating the principal transmitting components of a subscriber station of the stereoscopic video telecommunication system of the present invention.

FIG. 2 diagrammatically illustrates the principal transmitting components 21 of a wideband station 3. A left video camera unit 23 and a right video camera unit 24 form a stereoscopic camera assembly 25 and are optically converged on a subject to provide a pair of analog stereoscopic video signals representing a stereoscopic image or view of the subject. The individual left and right video signals are digitized by respective left and right analog to digital converters (ADC) 26 and 27. The video signals generated by the left and right cameras 23 are synchronized by a common synchronization generator circuit (SYNC GEN) 28. The left and right ADC'S 26 and 27 are coordinated or synchronized by a common sample clock 29 which is synchronized to the video frames from the cameras 23 and 24 by a signal derived from the sync generator 28. The sample clock 29 coordinates the digitization of the video signals and functions as a timing reference for other circuitry of the transmitting components 21.

The transmitting components 21 include left and right microphones 31 and 32 which are connected through suitable audio amplifiers 33 and 34 to respective analog to digital converters 35 and 36. The microphones 31 and 32 form a stereophonic microphone set 37 to generate a stereophonic audio signal or signal pair. A telephone microphone 39 of the telephone set 16 is connected through an audio amplifier 40 to a telephone analog to digital converter 41. The UART 17 converts data outgoing from the computer 14 from a parallel format to a serial format and converts incoming data to the computer 14 from serial to parallel. The UART 17 receives a clock reference from the sample clock 29.

The analog to digital converters 26, 27, 35, 36, and 41, along with the UART 17 of the computer 14, are all connected to a multiplexer (MUX) 43 which time-division multiplexes the digital signals from the various transmitting components 21, in relation to a data frame reference or frame flag 45 which is derived from the sample clock 29, for conversion of the electrical bit stream from the multiplexer 43 to a stream of light pulses by an optical fiber transmitter 47. The fiber transmitter 47 is connected to the network 2 by a transmitting optical fiber 48. The transmitting components 21 can incorporate compression circuitry (not shown) between the analog to digital converters 26 and 27, particularly, and the multiplexer 43 to reduce to overhead required on the network 2 by the video signals from the cameras 23 and 24. There are standard video compression routines and hardware available which can reduce the number of bits required to represent moving video images by factors of one hundred to one and greater, with little loss in detail. Such compression routines and hardware would be known to those skilled in the pertinent arts. The camera assembly 25, sync generator 28, microphones 37, and amplifiers 33 and 34 form the stereo audio/video source 7 shown in FIG. 1. The analog to digital converters 26, 27, 35, and 36 generally form the source interface 9. The sample clock 29, frame flag circuitry 45, multiplexer 43, and fiber transmitter 47 generally form a transmitting part of the network interface 10.

Figure 3:
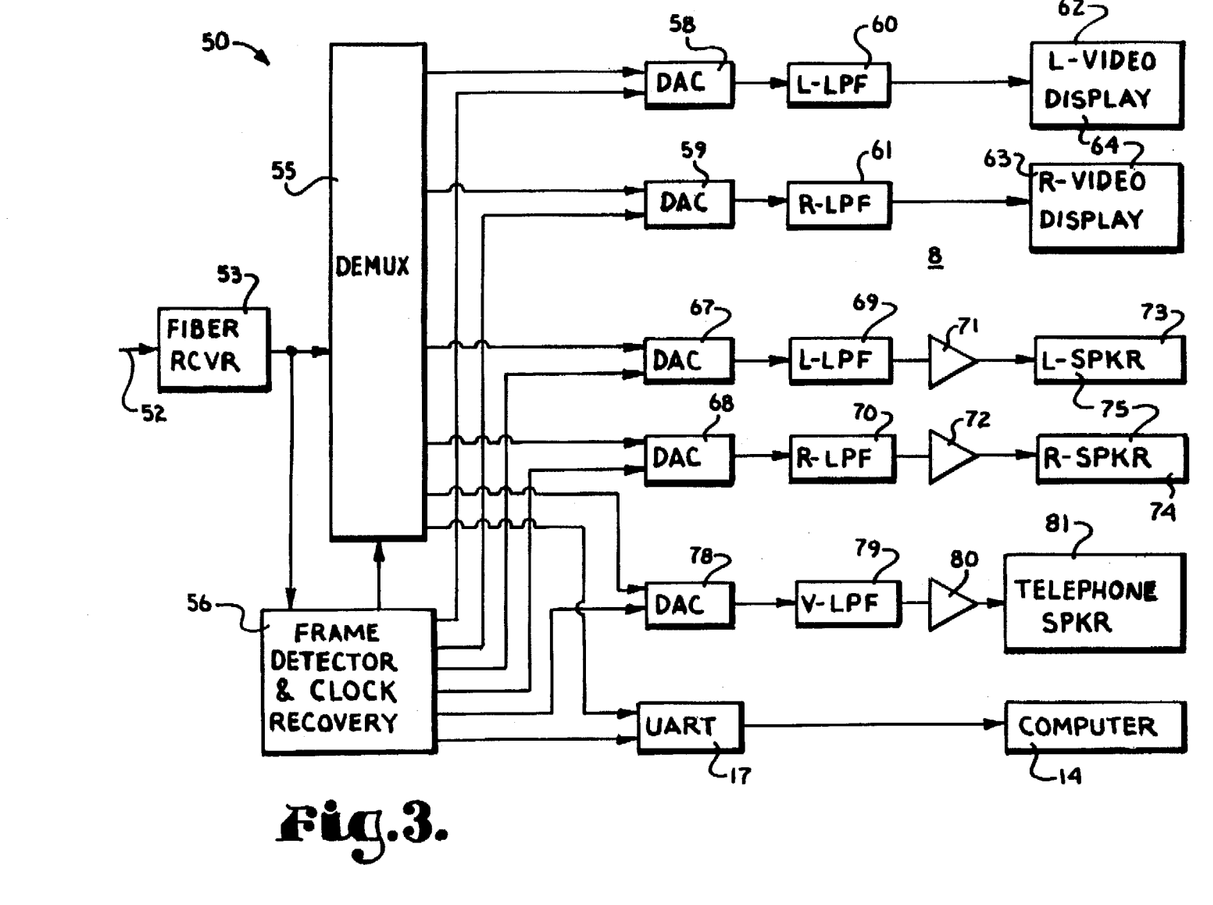
FIG. 3 is a block diagram illustrating the principal receiving components of the telecommunication system of the present invention.

Each wideband station 3 also includes receiving components 50 which are shown in more detail in FIG. 3. The receiving components 50 are coupled to the network 2 by a receiving optical fiber 52 through fiber receiving circuitry 53 which converts the light pulses on the receiving fiber 52 to an electrical bit stream. A demultiplexer (DEMUX) 55 separates digital data for the various devices of the receiving components 50 in relation to a frame reference derived from the bit stream by frame detector and clock recovery circuitry 56. It should be noted that successful operation of the system 1 depends on all stations 3 and 4 employing standardized communication protocols and data formats.

The components 50 include respective left and right video digital to analog converters 58 and 59 which are connected by respective filters 60 and 61 to left and right video displays or monitors 62 and 63. The converters 58 and 59 receive left and right digital video signals and, in cooperation with the filters 60 and 61 and as timed by clock signals from the clock recovery circuitry 56, convert the digital signals to analog video signals to drive the displays 62 and 63. The displays 62 and 63 form components of a stereoscopic video display 64. Alternatively, a single video display can be employed in cooperation with LCD shutters (not shown) in which left and right video frames or fields are alternately displayed in coordination with activation of the shutters, a technique which is employed in some types of stereoscopic displays.

Left and right stereophonic audio signals are recovered from the bit stream by left and right digital to analog converters 67 and 68, left and right low pass filters 69 and 70, audio power amplifiers 71 and 72, and left and right speakers 73 and 74. The speakers 73 and 74 may be combined to form a stereophonic audio output device 75, such as a pair of stereophonic headphones. In a similar manner, a conventional telephone audio signal is recovered by a digital to analog converter 78, a low pass filter 79, an audio amplifier 80, and a telephone speaker 81. The computer 14 receives telecommunicated data by way of the UART 17, which is bidirectional and can process data in either an outgoing or incoming direction. The frame detector and clock recovery circuitry 56 provides clock references for the digital to analog converters 58, 59, 67, 68, and 78, and the UART 17. In the receiving components 50, the video displays 64, speakers 75, and amplifiers 71 and 72 form the stereo audio/video receiver 8 of FIG. 1. The receiver interface 11 is generally formed by the digital to analog converters 58, 59, 67, 68, and associated filters 60, 61, 69, and 70. The fiber receiver 53, demultiplexer 55, and frame detector and clock recovery circuitry 56 form a receiving part of the network interface 10 of the generalized system shown in FIG. 1.

Figures 4, 5:
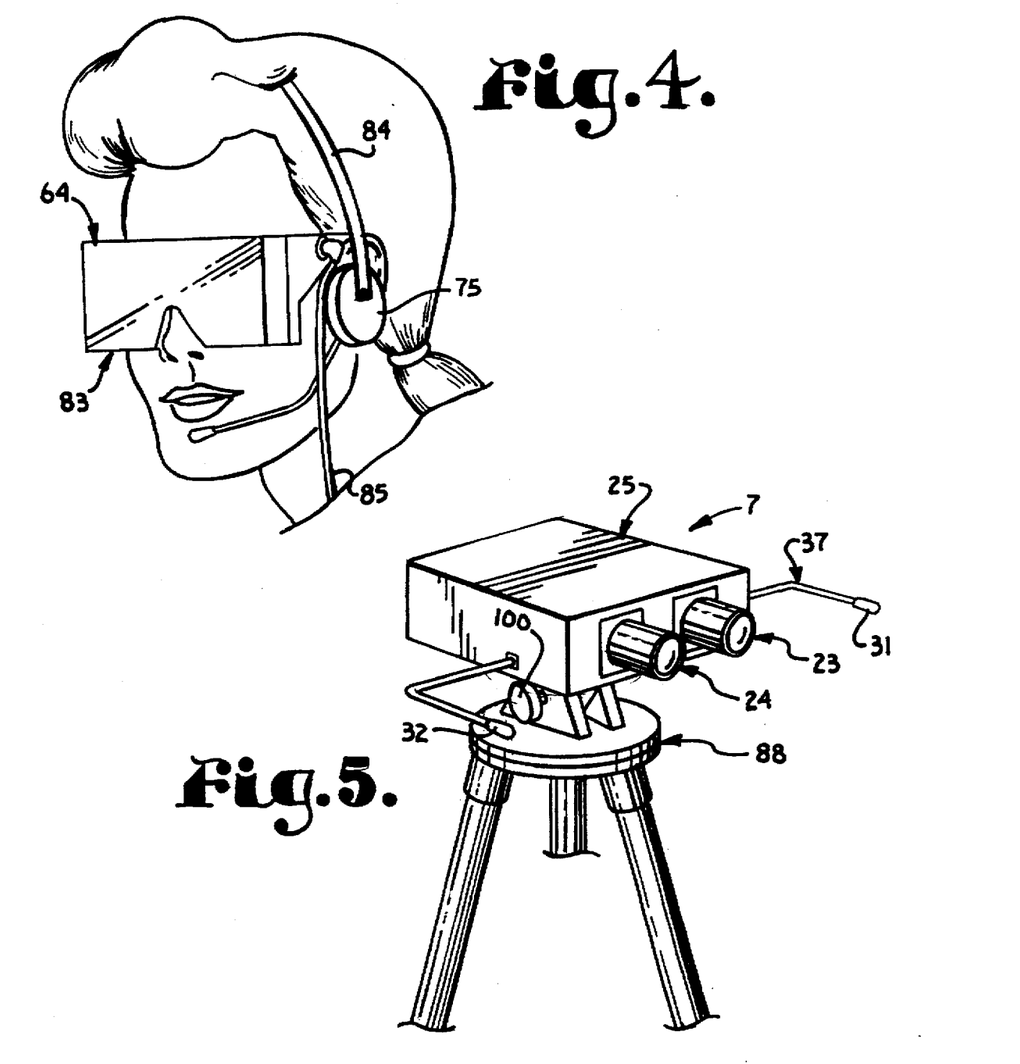
FIG. 4 is a perspective view of an exemplary head supported stereoscopic video display for use in the system of the present invention.
FIG. 5 is a perspective view of an exemplary stereoscopic video camera with stereophonic microphones for use in the system of the present invention.

FIG. 4 illustrates an exemplary headworn stereo audio/video output device 83 which may be used for viewing stereoscopic video and hearing stereophonic audio. The device 83 incorporates the stereoscopic video display pair 75. Preferably, the displays 64 are in the form of color liquid crystal displays (LCD's) along with suitable close focusing optics (not shown). The speaker pair 75 are mechanically interconnected by a resilient headband 84 which supports the device 83 on the head of a user. Signals to the displays 64 and 75 are received from the stereo audio/video receiver 8 by means of a cable 85. The device 83 may include a user microphone 86 for telephonic communication over the telephone set 16 or for voice-recognition commands to control the source 7, receiver 8, or computer 14 by circuitry not detailed herein.

Figure 6:
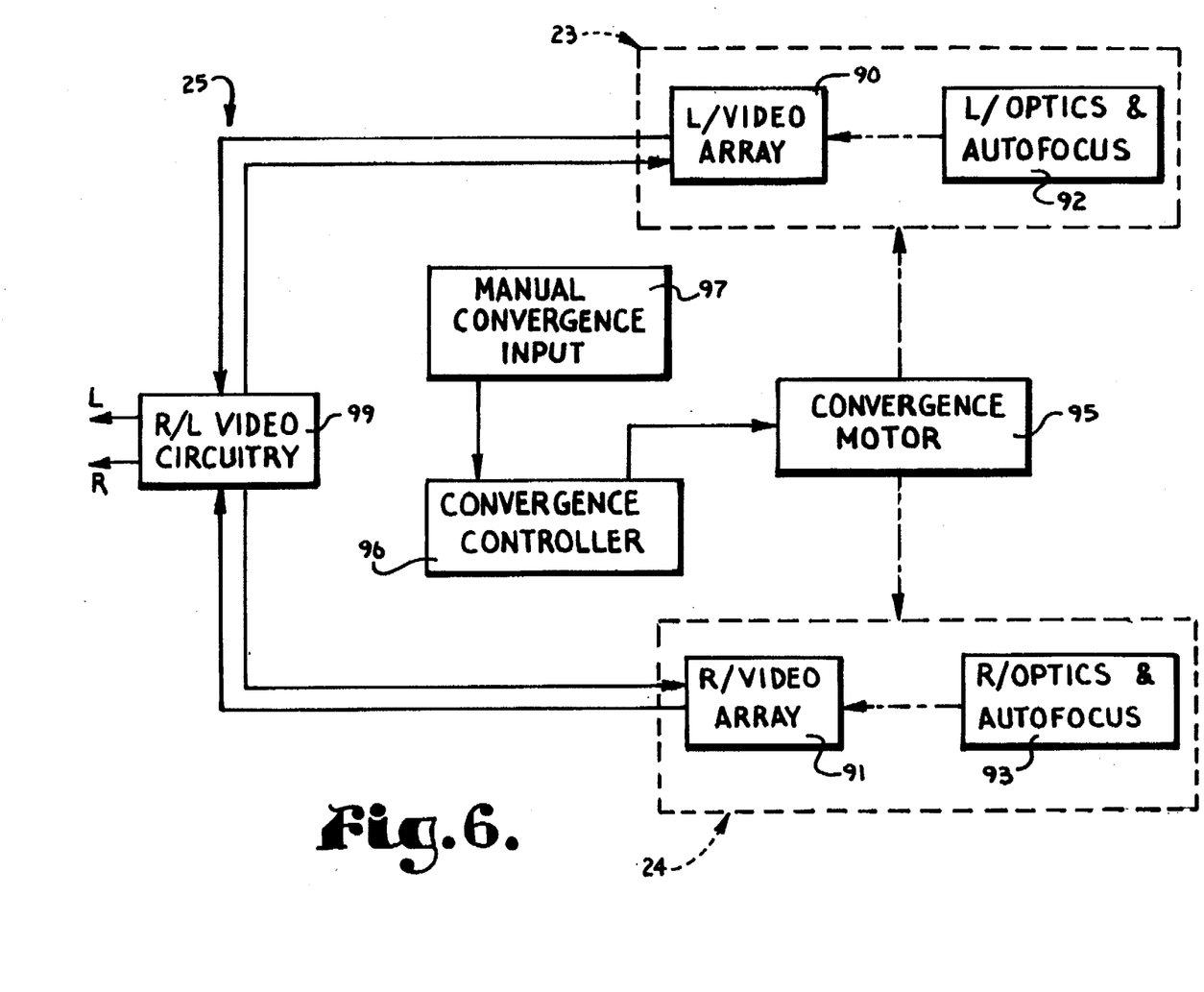
FIG. 6 is a simplified block diagram illustrating components of a stereoscopic video camera for use in the system of the present invention.

FIGS. 5 and 6 illustrate an exemplary audio/video source 7 including the stereoscopic camera assembly 25, an articulated camera support 88 such as a tripod, and stereophonic microphones 31 and 32. Each of the cameras 23 and 24 includes a respective video sensor array 90 or 91 (FIG. 6) along with a respective optics and autofocus unit 92 or 93. The camera units 23 and 24 are pivotally mounted and mechanically interconnected to a convergence motor 95 for coordinated converging of the optical axes of the camera units 23 and 24 at a common range. This is especially desirable at closer subject ranges so that the cameras 23 and 24 can properly scan a scene or subject stereoscopically. Operation of the convergence motor 95 is controlled by a convergence controller 96. The convergence distance can be set manually by a manual convergence input 97. Alternatively, the convergence controller 96 may receive inputs from the autofocus units 92 and 93. The video arrays 90 and 91 are preferably color capable and are controlled by conventional video circuitry 99, which may include the sync generator 28. The arrays 90 and 91 provide left and right analog video signals to the circuitry 99 for conversion to a desired standard video format.

The use of stereoscopic video is more appropriate in scientific, industrial, and medical applications where the higher cost of wideband services can be justified by the importance of the work involved. An exemplary use of the system 1 employing stereoscopic video is in communicating stereoscopic images of a surgical procedure, as for teaching or consultative purposes. A video library of recorded stereoscopic images of subjects, such as surgical procedures, may be recorded, for example using a type of stereoscopic laser disc system similar to that disclosed in U.S. Pat. No. 4,706,117, which is incorporated herein by reference. A wideband station 3 could be employed to access such procedures from such a library. Although not illustrated in FIG. 2, the transmitting components 21 could include a stereoscopic video playback device. Similarly, the receiving components 50 could include a stereoscopic recording device.

In many wideband subscriber stations 3, stereoscopic video is not required and may be configured with monoscopic or conventional two-dimensional video capabilities with either monophonic or stereophonic audio capability. Such a monoscopic wideband station 3 would be appropriate for most telephonic communication with the addition of monoscopic video transmission of images of the conversing parties. Such monoscopic capabilities would also be appropriate for the distribution of conventional video recordings of motion pictures.

It is to be understood that while certain forms of the present invention have been illustrated and described herein, it is not to be limited to the specific forms or arrangement of parts described and shown.

What is claimed and desired to be secured by Letters Patent is as follows:

1. A remote imaging system comprising:
   (a) a stereoscopic video signal source providing a stereoscopic video signal representing a full motion stereoscopic image;
   (b) a communication network;
   (c) source interface means coupling said video source to said network;
   (d) video display means positioned remote from said source and operable to display images derived from said video signal;
   (e) display interface means coupling said display means to said network to enable reception by said display means of said video signal communicated over said network from said source; and
   (f) said video signal source, said communication network, and said video display means cooperating to communicate said signal representing a full motion stereoscopic image from said video signal source to said video display means in substantially real time.

2. A system as set forth in claim 1 and including:
   (a) a first station including said stereoscopic video signal source which is a first stereoscopic video signal source and which provides a first stereoscopic video signal, said video display means which is a first video display means, and first network interface means coupling said first video source and said first display means to said network;
   (b) a second station remote from said first station and including a second stereoscopic video signal source similar to said first stereoscopic video signal source and providing a second stereoscopic video signal, a second video display means similar to said first video display means, and second network interface means coupling said second video source and said second display means to said network; and
   (c) said first and second network interface means cooperating with said network to provide substantially duplex communication of said first video signal to said second video display means and said second video signal to said first video display means.

3. A system as set forth in claim 2 and including:
   (a) a first audio signal source positioned at said first station and providing a first audio signal;
   (b) a first audio signal receiver positioned at said first station and operable to audibly play an audio signal received thereby;
   (c) said first network interface means coupling said first audio signal source and said first audio signal receiver to said network;
   (d) a second audio signal source positioned at said second station and providing a second audio signal;
   (e) a second audio signal receiver positioned at said second station and operable to audibly play an audio signal received thereby;
   (f) said second network interface means coupling said second audio signal source and said second audio signal receiver to said network; and
   (g) said first and second network interface means cooperating with said network to provide substantially duplex communication of said first audio signal to said second audio receiver and said second audio signal to said first audio receiver.

4. A system as set forth in claim 3 wherein:
   (a) each of said audio signal sources and said audio signal receivers is stereophonic.

5. A system as set forth in claim 2 wherein each of said network interface means includes:
   (a) dialer means enabling the establishment of a communication link by one of said stations, over said network, with the other of said stations.

6. A system as set forth in claim 2 and including:
   (a) a first telephone set coupled to said first network interface means;
   (b) a second telephone set coupled to said second network interface means; and
   (c) said first and second network interface means cooperating with said network to enable conventional telephone communications between said first and second stations.

7. A system as set forth in claim 1 wherein:
   (a) said stereoscopic video signal source provides a video signal representing a moving stereoscopic image.

8. A system as set forth in claim 1 wherein:
(a) said communication network includes a fiberoptic wideband switching network.

9. A system as set forth in claim 1 wherein:
(a) said video display means is a stereoscopic video display means operable to display said stereoscopic image represented by said stereoscopic video signal.

10. A system as set forth in claim 1 wherein said video display means includes:
(a) a head supported stereoscopic video display.

11. A remote imaging system comprising:
(a) a communication network;
(b) a first station including:
 (1) a first stereoscopic video signal source providing a first stereoscopic video signal representing a first full motion stereoscopic image;
 (2) a first video display means operable to display images derived from a video signal;
 (3) a first audio signal source positioned at said first station and providing a first audio signal;
 (4) a first audio signal receiver positioned at said first station and operable to audibly play an audio signal received thereby; and
 (5) first network interface means coupling said first video source, said first display means, said first audio signal source, and said first audio signal receiver to said network;
(c) a second station including:
 (1) a second stereoscopic video signal source providing a second stereoscopic video signal representing a second full motion stereoscopic image;
 (2) a second video display means operable to display images derived from a video signal;
 (3) a second audio signal source positioned at said second station and providing a second audio signal;
 (4) a second audio signal receiver positioned at said second station and operable to audibly play an audio signal received thereby; and
 (5) second network interface means coupling said second video source, said second display means, said second audio signal source, and said second audio signal receiver to said network;
(d) said first and second network interface means cooperating with said network to provide substantially duplex communication of said first video signal to said second video display means, said first audio signal to said second audio signal receiver, said second video signal to said first video display means, and said second audio signal to said first audio signal receiver.

12. A system as set forth in claim 11 wherein each station includes:
(a) analog to digital converter (ADC) means coupled between each video signal source and each audio signal source and the associated network interface means, said ADC means converting an analog signal from said video signal source and audio signal source to a digital signal for communication on said network.

13. A system as set forth in claim 11 wherein each station includes:
(a) digital to analog converter (DAC) means coupled between said network interface means and the associated video display and the associated audio signal receiver, said DAC means converting a digital signal communicated from said network to a respective analog signal for use by said video display and said audio signal receiver.

14. A system as set forth in claim 11 wherein:
(a) each of said audio signal sources and said audio signal receivers is stereophonic.

15. A system as set forth in claim 11 wherein each of said network interface means includes:
(a) dialer means enabling the establishment of a communication link by one of said stations, over said network, with the other of said stations.

16. A system as set forth in claim 11 and including:
(a) a first telephone set coupled to said first network interface means;
(b) a second telephone set coupled to said second network interface means; and
(c) said first and second network interface means cooperating with said network to enable conventional telephone communications between said first and second stations.

17. A system as set forth in claim 11 wherein:
(a) said communication network includes a fiberoptic wideband switching network.

18. A system as set forth in claim 11 wherein:
(a) each of said video display means is a stereoscopic video display means operable to display said stereoscopic image represented by said stereoscopic video signal.

19. A system as set forth in claim 11 wherein:
(a) at least one of said video display means includes a head supported stereoscopic video display.

20. In a wideband communication network operable to route wideband signals, including signals representing video images, between stations interconnected by said network, the improvement comprising:
(a) a first stereoscopic video signal source positioned at a first station and providing a first stereoscopic video signal representing a first full motion stereoscopic image;
(b) first video display means positioned at said first station and operable to display images derived from a video signal;
(c) first network interface means coupling said first video source and said first video display means to said wideband communication network;
(d) a second stereoscopic video signal source positioned at a second station and providing a second stereoscopic video signal representing a second full motion stereoscopic image;
(e) second video display means positioned at said second station and operable to display images derived from a video signal;
(f) second network interface means coupling said second video signal source and said second display means to said network; and
(g) said first and second network interface means cooperating with said network to provide substantially duplex communication of said first video signal to said second video display means and said second video signal to said first video display means over said network.

21. A system as set forth in claim 20 wherein:
(a) each of said video display means is a stereoscopic video display means.

22. A system as set forth in claim 20 wherein:
(a) at least one of said video display means includes a head supported stereoscopic video display.

23. A system as set forth in claim 20 wherein each of said network interface means includes:
   (a) dialer means enabling the establishment of a communication link by one of said stations, over said network, with the other of said stations.

24. A system as set forth in claim 20 and including:
   (a) a first telephone set coupled to said first network interface means;
   (b) a second telephone set coupled to said second network interface means; and
   (c) said first and second network interface means cooperating with said network to enable conventional telephone communications between said first and second stations.

* * * * *